United States Patent

Onan et al.

[11] Patent Number: 6,055,874
[45] Date of Patent: May 2, 2000

[54] APPARATUS AND METHOD FOR SIMULATING WELL BORE CONDITIONS

[75] Inventors: David D. Onan, Duncan; Dennis W. Gray, Comanche; Russell M. Fitzgerald; Johnny W. Johnson, both of Duncan, all of Okla.

[73] Assignee: Halliburton Energy Services, Inc., Duncan, Okla.

[21] Appl. No.: 09/243,322

[22] Filed: Feb. 2, 1999

[51] Int. Cl.⁷ .................................................. G01N 1/00
[52] U.S. Cl. ......................................................... 73/865.6
[58] Field of Search ................................ 73/53, 38, 865.6

[56] References Cited

U.S. PATENT DOCUMENTS

| | | | |
|---|---|---|---|
| 3,286,510 | 11/1966 | Parker | 73/53 |
| 4,259,868 | 4/1981 | Rao et al. | 73/597 |
| 4,380,266 | 4/1983 | Wellington | 166/252 |
| 4,409,662 | 10/1983 | Rao | 364/364 |
| 4,430,889 | 2/1984 | Sutton | 73/61.4 |
| 4,567,765 | 2/1986 | Rao et al. | 73/594 |
| 4,648,264 | 3/1987 | Freese et al. | 73/64.1 |
| 4,691,558 | 9/1987 | Vinson et al. | 73/64.1 |
| 4,700,567 | 10/1987 | Frey et al. | 73/151 |
| 4,780,858 | 10/1988 | Clerke | 367/35 |
| 4,823,594 | 4/1989 | Gray | 73/54 |
| 5,209,104 | 5/1993 | Collins et al. | 73/38 |
| 5,309,761 | 5/1994 | Ravi et al. | 73/865.16 |
| 5,325,723 | 7/1994 | Meadows et al. | 73/794 |
| 5,329,811 | 7/1994 | Schultz et al. | 73/155 |

OTHER PUBLICATIONS

Application Serial No. 09/166,456, filing date Oct. 6, 1998 entitled "Dynamic Fluid Loss Cell Apparatus and Method Thereof".

J. V. Fisk et al.: "The Use of Filtration Theory In Developing A Mechanism For Filter–Cake Deposition By Drilling Fluids In Laminar Flow," SPE Drilling Engineering, Sep. 1991, pp. 196–202.

Marlo Zamora et al.: "Innovative Devices For Testing Drilling Muds," SPE Driling Engineering, Mar. 1990, pp. 11–16.

B. G. Chesser et al.: "Dynamic And Static Filtrate–Loss Techniques For Monitoring Filter–Cake Quality Improved Drilling–Fluid Performance," SPE Drilling & Conference, Mar. 18, 1994.

*Primary Examiner*—Robert Raevis
*Attorney, Agent, or Firm*—Craig E. Roddy; C. Clark Dougherty, Jr.

[57] ABSTRACT

The present invention provides methods and apparatus for simulating well bore conditions before and after cementing therein. The methods of the invention are basically comprised of the steps of circulating a drilling fluid through a closed test cell containing a permeable rock core while maintaining a selected pressure differential across the rock core to form a layer of filter cake thereon, circulating a filter cake removal fluid through the test cell to simulate the clean-up of the well bore and then determining the condition of the rock core with respect to the effectiveness of the filter cake removal fluid thereon.

17 Claims, 2 Drawing Sheets

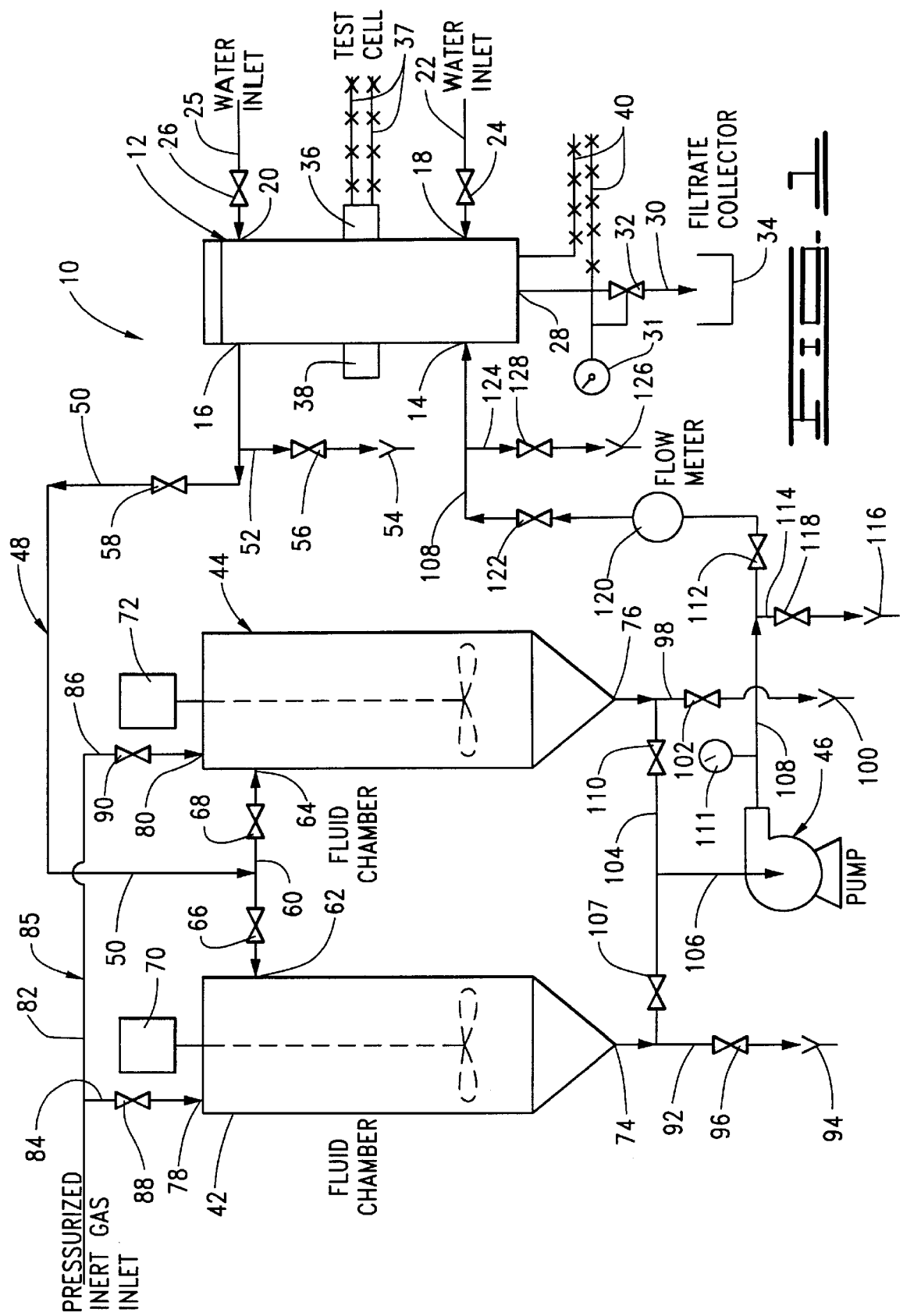

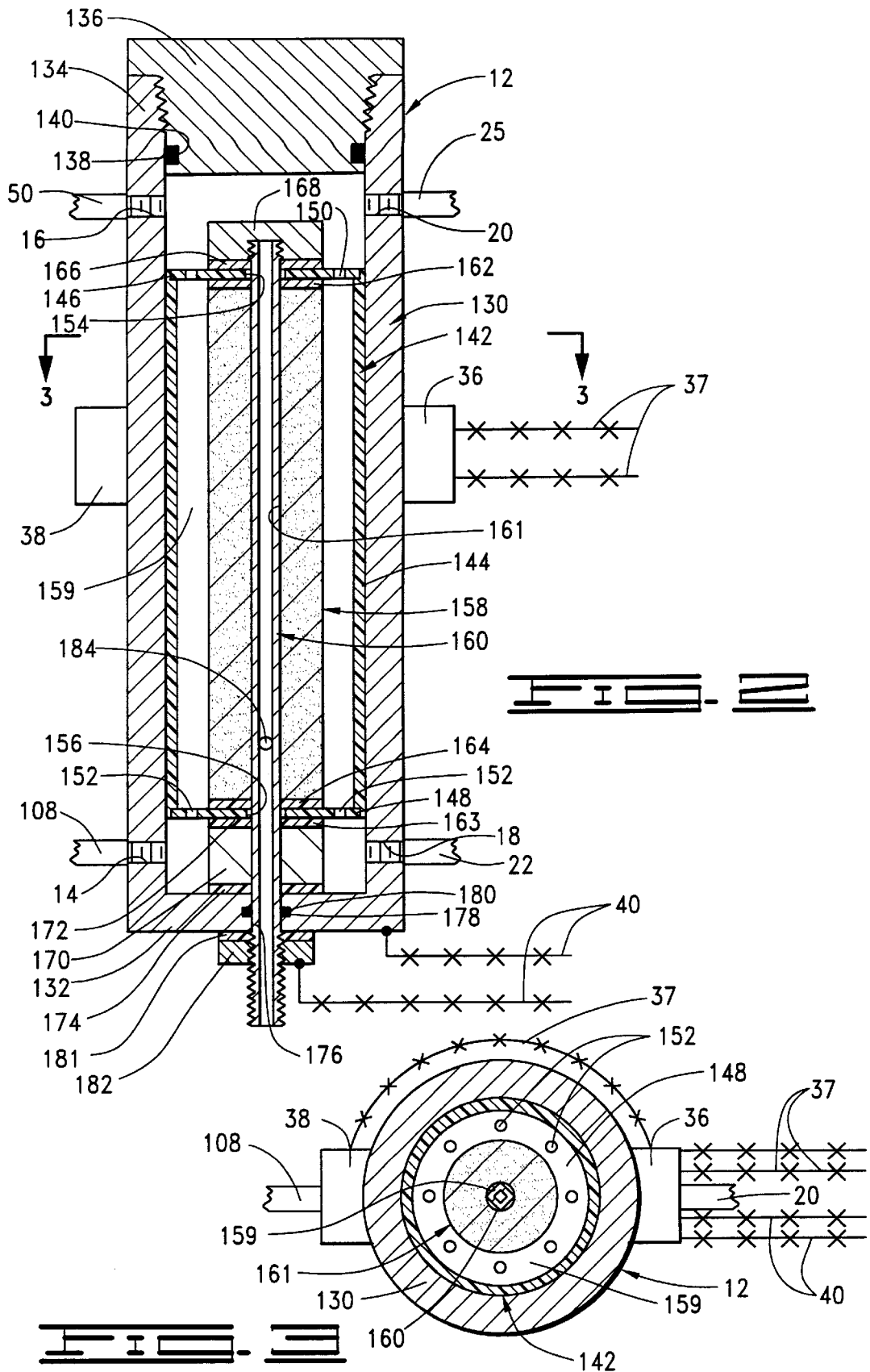

APPARATUS AND METHOD FOR SIMULATING WELL BORE CONDITIONS

BACKGROUND OF THE INVENTION

1. Field of the Invention.

This invention relates to methods and apparatus for simulating well bore conditions before and after cementing therein.

2. Description of the Prior Art.

A variety of drilling fluids are used in the drilling of well bores. Generally, the fluids are solids containing water based gels or hydrocarbon based fluids which can be non-weighted or weighted with particulate weighting materials such as barite. Most drilling fluids contain gelled bentonite and/or one or more natural or synthetic polymeric additives such as polysaccharides or polysaccharide derivatives. The polymeric additives add viscosity to the fluid and are included to impart sufficient carrying capacity and thixotropy whereby the fluids can transport cuttings to the surface and prevent the cuttings from settling appreciably when circulation is interrupted. Natural and synthetic polymeric fluid loss control additives are also commonly utilized in drilling fluids, e.g., polysaccharides, polysaccharide derivatives, polyacrylic acids, polyvinyl alcohol and the like.

One of the most important functions of a drilling fluid is to seal off the walls of the well bore so that the drilling fluid is not lost into highly permeable subterranean zones penetrated by the well bore. This is accomplished by the deposit of a filter cake of solids from the drilling fluid, dehydrated drilling fluid and gelled drilling fluid over the surfaces of the well bore whereby the solids bridge over the formation pores and do not permanently plug the pores. During the drilling of a well bore, the drilling fluid is continuously circulated down the drill pipe, through the drill bit and back to the surface through the annulus between the drill pipe and the walls of the well bore. After a well bore reaches total depth, the circulation of the drilling fluid is stopped while the well is logged and a pipe string, e.g., casing or a liner is run in the well bore. During the shut down period, additional gelled and dehydrated drilling fluid and filter cake are deposited on the walls of the well bore. As a result of the polymeric viscosifiers and additives in the drilling fluid, the filter cake formed is generally very stable and difficult to remove.

After a string of pipe is run in the well bore, primary cementing operations are usually performed therein. That is, the string of pipe is sealed in the well bore by placing a cement composition in the annulus between the pipe and the walls of the well bore. The cement composition sets into a hard impermeable mass and it is intended to bond the pipe to the walls of the well bore whereby the annulus is sealed and fluid communication between subterranean zones or to the surface by way of the annulus is prevented. However, in order for the cementing of the pipe in the well bore to be successful, the filter cake comprised of gelled and dehydrated drilling fluid and solids deposited on the walls of the well bore must be removed. If appreciable filter cake remains on the walls of the well bore, the cement composition utilized will not properly bond thereto and fluid leakage through the annulus and other major problems will result.

Heretofore, flushes have been pumped through the annulus between the pipe and the walls of the well bore prior to cementing in order to remove filter cake therefrom. The flushes have been pumped through the annulus at high rates so that they are in turbulence as they contact the filter cake, and surfactants have been included in the flush fluids to lower surface tension and enhance the penetration of the flush fluids into the filter cake. While these methods have been believed to achieve success, the only measure of that success has been the subsequent detection or non-detection of annulus leaks over time.

Thus, there are needs for apparatus and methods that can quickly and easily be utilized for testing the effectiveness of flush fluids in removing filter cake from well bores as well as the strengths of the subsequent bonds obtained between cement compositions and the walls of the well bores.

SUMMARY OF THE INVENTION

The present invention provides apparatus and methods for simulating well bore conditions before and after cementing which meet the needs described above and overcome the deficiencies of the prior art. The apparatus and methods can be utilized in laboratories to quickly and easily determine the effectiveness of flush fluids in removing drilling fluid and filter cake from well bores whereby strong bonds between the cement compositions to be used and the walls of the well bores will result.

The apparatus of the present invention basically comprises a closeable elongated test cell having at least one inlet connection and one outlet connection formed therein at opposite ends thereof. A removable elongated insert is disposed within the test cell containing an elongated hollow permeable rock core having a cross sectional periphery smaller than the inside cross section of the insert. The ends of the insert are closed by perforated plates in sealing contact with the ends of the rock core whereby a fluid flowing through the test cell and through the insert therein contacts only the outside surfaces of the rock core. A filtrate removal tube having at least one opening therein is disposed within the interior of the rock core which sealingly extends through the insert and the test cell whereby filtrate from the fluid on the outside of the rock core which passes through the rock core by way of its permeability flows out of the test cell by way of the tube to a place of collection. A system of conduits and valves is connected to a source of at least one test fluid and to the inlet and outlet connections of the test cell for selectively circulating the test fluid through the test cell, and a pump is disposed in the conduit and valve system for causing the test fluid to flow through the conduit and valve system and the test cell at a selected flow rate.

The methods of this invention for simulating the conditions in a well bore before and after cementing therein are basically comprised of the steps of circulating a drilling fluid through a closed test cell containing a permeable rock core while maintaining a desired flow rate and pressure differential across the rock core until a layer of filter cake is formed on the rock core, circulating a filter cake removal fluid through the test cell to simulate the clean up of the well bore prior to performing cementing operations therein, and then determining the condition of the rock core with respect to the effectiveness of the filter cake removal fluid thereon.

It is, therefore, a general object of the present invention to provide test apparatus and methods for simulating well bore conditions before and after cementing.

Other and further objects, features and advantages of the present invention will be readily apparent to those skilled in the art upon a reading of the description of preferred embodiments which follows.

BRIEF DESCRIPTION OF THE DRAWINGS

FIG. 1 is a schematic illustration of the apparatus of the invention for simulating well bore conditions.

FIG. 2 is an enlarged cross sectional view of the test cell of FIG. 1.

FIG. 3 is a cross sectional view taken along line 3—3 of FIG. 2.

DESCRIPTION OF PREFERRED EMBODIMENTS

As mentioned, this invention provides test apparatus and methods for simulating well bore conditions before and after cementing using a selected drilling fluid, a selected filter cake removal fluid and a selected cement composition. For example, the apparatus and methods can be quickly and easily utilized in the laboratory for determining the most effective filter cake removal fluid after a well bore has been drilled. Also, the most effective cement composition for use in combination with the selected removal fluid can be determined.

The Apparatus

Referring now to the drawings and particularly to FIG. 1, the apparatus of the present invention is illustrated and generally designated by the numeral 10. The apparatus 10 includes a closeable elongated test cell 12 having at least one test fluid inlet connection 14 at its lower end portion and at least one test fluid outlet connection 16 at its upper end portion. Water inlet connections 18 and 20 are also provided in the lower and upper end portions of the test cell 12, respectively, opposite the connections 14 and 16. A conduit 22 having a shut-off valve 24 disposed therein is connected between the water inlet connection 18 and a source of water (not shown). A conduit 25 having a shut-off valve 26 disposed therein is connected between the water inlet connection 20 and the source of water (not shown). The test cell 12 also includes a filtrate outlet connection 28 at its lower end which is connected to a filtrate removal conduit 30 having a pressure gage 31 and a back pressure regulator 32 disposed therein. The conduit 30 leads filtrate withdrawn from the test cell 12 to a filtrate collecting and measuring container 34.

As will be described further hereinbelow, the test cell 12 includes a pair of sonic transducers 36 and 38 for generating filter cake thickness and cement composition integrity measurements. A pair of electric leads 37 are connected to the transducers 36 and 38 and to one or more electronic components (not shown) for processing the sonic information and providing thickness and integrity measurement readouts. The test cell 12 also includes electrodes connected to electric leads 40 which are in turn connected to one or more electronic components (not shown) for measuring the resistivity of the fluid in the test cell and thereby detecting the presence of oil in the test cell.

A pair of closeable, heated (heating elements not shown) mixing chambers 42 and 44 are provided for containing and heating (if desired) drilling fluid, water, and a cement composition. Also provided is a pump 46 for circulating fluid from one of the chambers 42 or 44 through the test cell 12 by way of a system of conduits and valves generally designated by the numeral 48. Starting at the outlet connection 16 of the test cell 12, the system of conduits and valves 48 is comprised of a conduit 50 connected to the outlet connection 16. A conduit 52 is connected to the conduit 50 and to a drain or other waste disposal location 54 and a shut-off valve 56 is disposed in the conduit 52. A shut-off valve 58 is disposed in the conduit 50 downstream of the conduit 52 and the opposite end of the conduit 50 from the connection 16 in the test cell 12 is connected to a conduit 60.

The opposite ends of the conduit 60 are connected to inlet connections 62 and 64 in the chambers 42 and 44, respectively. A shut-off valve 66 is disposed in the conduit 60 between the inlet connection 62 of the chamber 42 and the conduit 50 and a shut-off valve 68 is connected in the conduit 60 between the conduit 50 and the inlet connection 64 of the chamber 44.

Each of the closeable chambers 42 and 44 include mixing devices 70 and 72 sealingly attached thereto, respectively, for constantly mixing drilling fluids, cement compositions and the like contained therein. The chambers 42 and 44 also include outlet connections 74 and 76 at the lower ends thereof, respectively. In addition, the chambers 42 and 44 include pressurized inert gas inlet connections 78 and 80, respectively. A second system of conduits and valves 85 is provided comprised of a conduit 82 connected to a source of pressurized inert gas, preferably nitrogen, and conduits 84 and 86 connected between the conduit 82 and the inert gas inlet connections 78 and 80 of the chambers 42 and 44. shut-off valves 88 and 90 are disposed in the conduits 84 and 86, respectively.

A conduit 92 is connected to the outlet connection 74 of the chamber 42 and to a drain or other waste disposal location 94. A shut-off valve 96 is disposed in the conduit 92. In a like manner, a conduit 98 is connected to the outlet connection 76 of the chamber 44 and to a drain or other waste disposal location 100 and a shut-off valve 102 is disposed in the conduit 98. A conduit 104 is connected to the conduits 92 and 98 at points between the outlet connections 74 and 76 of the chambers 42 and 44 and the shut-off valves 96 and 102 therein. A conduit 106 is connected to the conduit 104 and to the suction connection of the pump 46. A shut-off valve 107 is disposed in the conduit 104 between the conduit 92 and the conduit 106. In a like manner, a shut-off valve 110 is disposed in the conduit 104 between the conduit 106 and the conduit 98.

The discharge connection of the pump 46 is connected by a conduit 108 to the inlet connection 14 of the test cell 12. From the pump end of the conduit 108, it includes a pump discharge pressure gage 110 connected thereto and a shut-off valve 111 disposed therein. A conduit 114 is connected to the conduit 108 upstream of the shut-off valve 112 and to a drain or other waste disposal location 116. A shut-off valve 118 is disposed in the conduit 114. A flow meter 120 is disposed in the conduit 108 downstream of the shut-off valve 112, and a shut-off valve 122 is disposed in the conduit 108 downstream of the flow meter 120. A conduit 124 is connected to the conduit 108 between the shut-off valve 122 and the inlet connection 14 of the test cell 12 and to a drain or other waste disposal location 126. A shut-off valve 128 is disposed in the conduit 124.

Referring now to FIGS. 2 and 3, the test cell 12 is illustrated in greater detail. The test cell 12 is comprised of an elongated, preferably cylindrical housing 130 having a closed bottom end 132 and an open internally threaded top end 134. A threaded closure 136 which includes an O-ring seal member 138 disposed in a complimentary groove 140 is threadedly connected to the upper end 134 of the housing 130.

The upper end portion of the housing 130 includes the previously described test fluid outlet connection 16 having the conduit 50 connected thereto and the previously described water inlet connection 20 having the conduit 25 connected thereto. The bottom end portion of the housing 130 includes the previously described test fluid inlet connection 14 having the conduit 108 connected thereto and the previously described water inlet connection 18 having the conduit 22 connected thereto. The sonic transducers 36 and 38 for measuring the thickness of filter cake and cement composition within the test cell 12 are connected to the housing 130 on opposite sides thereof. As best shown in FIG. 3, the electric leads 37 connect the transducers 36 and 38 together and to the previously described electronic control and read-out system (not shown).

Disposed within the housing 130 is a removable elongated preferably cylindrical insert generally designated by the numeral 142 which is formed of a material to which set cement compositions do not adhere. A presently preferred such material is selected from tetrafluoroethylene fluorocarbon polymers, fluorinated ethylene-propylene resin and copolymers of the aforesaid polymers and resins, all of which materials are commercially available under the trade name "TEFLON™" from DuPont of Wilmington, Del. The insert 142 is comprised of a solid sidewall 144 and a pair of removable perforated end plates 146 and 148. Both of the end plates 146 and 148 are perforated by a plurality of spaced openings 150 and 152, respectively, positioned in spaced relationship around the periphery of the end plates. The end plates 146 and 148 also include central openings 154 and 156 disposed therein, respectively.

Removably positioned between the insert end, plates 146 and 148 is a preferably cylindrical, hollow permeable rock core 158 having a cross sectional periphery smaller than the inside cross section of the insert 142 whereby an annular space 159 is provided between the rock core 158 and the insert 142. A tube 160 which is threaded at both ends is disposed within the interior opening 161 of the hollow core 158 and extends through the central openings 154 and 156 of the insert perforated end plates 146 and 148, respectively. A pair of sealing gasket members 162 and 163 are disposed between the ends of the permeable rock core 158 and the insert end plates 146 and 148, respectively.

A sealing gasket 166 is positioned on top of the insert end plate 146 and a tube closing and retaining member 168 is threadedly attached to the upper end of the tube 160. The lower end portion of the tube 160 which extends through the insert end plate 148 also extends through the interior of a spacer sleeve 170 having sealing gaskets 172 and 174 adjacent the top and bottom ends thereof and through an opening 176 positioned in the bottom end 132 of the housing 130. An O-ring seal member 178 is disposed in a complimentary groove 180 formed in the housing 130 within the opening 176 therein which provides a seal between the housing 130 and the tube 160. The portion of the tube 160 extending through the opening 176 of the housing 130 is threaded and a complimentary threaded retaining nut 182 along with an electricity insulating gasket 181 are attached thereto. As will now be understood, the retaining nut 182 and the retaining member 168 threadedly attached to the ends of the tube 160 rigidly hold the gaskets 162, 164, 166, 172, 174 and 181 in sealing contact with adjacent surfaces whereby the ends of the rock core 158 are sealed and a test fluid flowing through the test cell 12 and through the annular space 159 between the insert 142 and the rock core 158 contacts only the outside longitudinal surface of the rock core 158.

The portion of the tube 160 within the rock core 158 is smaller than the opening 161 therein (e.g., its cross-sectional shape can be square as shown in FIG. 3), and the tube 160 includes at least one lateral opening 184 therein whereby filtrate from the test fluid in contact with the outside surfaces of the rock core 158 which passes through the rock core 158 by way of its permeability is free to flow into the interior of the tube 160 by way of the opening 184 and out of the test cell 12 by way of the tube 160.

The electric leads 40 are electrically attached to the housing 130 and to the filtrate tube 160 by way of the nut 182 which are formed of electricity conducting metal and are insulated from each other. The leads 40 are connected to electronic apparatus (not shown) for measuring the electric resistivity of fluids in the test cell 12 to thereby determine the presence or non-presence of oil as will be further described hereinbelow.

Operation Of The Apparatus 10

As mentioned, the apparatus 10 can be utilized to evaluate the effects of fluid flow in contact with permeable rock having filter cake comprised of solids, gelled drilling fluid and dehydrated drilling fluid deposited thereon. For example, after depositing filter cake on a selected permeable rock core utilizing a selected drilling fluid, various flush fluids containing surfactants and other components for removing filter cake from the core can be circulated at various flow rates and pressures into contact with the filter cake. The thickness of the filter cake before and after being contacted with each flush fluid can be determined and a selected cement composition can be placed in the test cell after a selected flush fluid to determine the strength of the bond formed between the cement composition and the rock core.

In performing tests of the types described above and with all of the valves in the conduit and valve systems 48 and 85 initially closed, a quantity of water is placed in one of the fluid chambers, e.g., 42 with a quantity of a selected drilling fluid being placed in the other chamber, e.g., chamber 44. The chambers are closed and sealed and the stirring device 72 in the fluid chamber 44 is started to continuously mix the drilling fluid therein while it is being heated to a desired temperature. Thereafter, water is circulated through the test cell 12 at a selected pressure by opening valve 108, valve 112, valve 122, valve 58 and valve 66 and then starting the pump 46. After the desired flow rate through the test cell 12 is achieved, valve 88 is opened to allow inert gas to enter the fluid chamber 42 containing water until the desired discharge pressure from the pump 46 is indicated on the pressure indicator 110. The back pressure regulator valve 32 is next opened and set to produce a selected differential pressure across the permeable rock core within the test cell 12. The circulation of the water is then continued while filtrate is collected and measured in the filtrate collector 34 for a certain period of time. Using the pressure differential, the amount of filtrate collected and the time period over which the filtrate was collected, the permeability of the rock core in the test cell 12 is calculated. This can be accomplished manually or by a transducer and computer (not shown) in which the data is manually and/or automatically entered.

The pump 46 and water flow are shut-off and the inert gas pressure exerted on the fluid chamber containing water, i.e., fluid chamber 42, is relieved. Thereafter, valves 66, 108 and 58 are closed and valve 110 is opened. Inert gas pressure is then applied to the fluid chamber 44 containing the selected drilling fluid by opening the valve 90 and drain valve 56 is opened to allow the pressure within fluid chamber 44 to cause drilling fluid to enter the conduit and valve system and displace water from the conduit and valve system (except for the conduit 50), the pump 46 and the test cell 12 into the drain 54. Once the water has been displaced into the drain, valve 56 is closed and valves 58 and 68 are opened. The pump 46 is then started and circulation of drilling fluid through the test cell 12 is commenced at a desired flow rate. The back pressure regulator 32 is set to provide a desired pressure differential across the rock core and circulation of the drilling fluid is continued while filtrate is collected until a filter cake has formed on the rock core as indicated by diminished or terminated filtrate flow and a constant filtrate thickness read-out from the sonic thickness detector comprised of the transducers 36 and 38 and related equipment.

While the filter cake is being deposited on the rock core as described above, the water can be drained from the fluid chamber 42 by opening the chamber and the drain valve 96. Thereafter, the drain valve 96 can be closed and a selected flush fluid can be placed in the fluid chamber 42. When the filter cake has been deposited on the rock core and the flow of drilling fluid through the test cell 12 has been terminated, the pressure is relieved from the fluid chamber 44 and the valves 68 and 110 are closed. Thereafter, the valve 58 is closed, the drain valve 56 connected to the drain 54 is opened and inert gas pressure is applied to the fluid chamber 42 by opening the valve 88. The valve 107 is then opened and the drilling fluid in the conduit and valve system 48 (except for the conduit 50), in the pump 46 and in the test cell 12 is displaced by the flush fluid into the drain 54. Thereafter, the valve 58 is opened, the valve 66 is opened and the drain valve 56 is closed. The pump 46 is started so that the flush fluid is circulated through the test cell 12 and into contact with the filter cake on the rock core therein. The flow rate of the flush fluid being circulated is set at a desired rate and the flush fluid is allowed to circulate for a selected period of time or for the time period required to substantially remove the filter cake from the rock core as determined by the sonic thickness testing equipment.

If desired, after circulating the flush fluid and after the pressure on the system has been relieved, the shut-off valves 58 and 122 can be closed and the test cell 12 can be opened by removing the closure 136 therefrom. The threaded nut 182 is then removed from the filtrate tube 160 and the insert assembly 142 including the rock core can be removed from the test cell 12 and examined visually to determine the extent of filter cake removal, etc.

In an alternate procedure, after the flush fluid has been circulated to remove the filter cake from the rock core, the valves 66 and 107 can be closed and after pressure has been relieved, the fluid chamber 42 can be opened along with the drain valve 96 to drain the flush fluid from the chamber 42. Thereafter, the chamber 42 can be cleaned and filled with a cement composition, reclosed and sealed and the mixer 70 turned on to continuously mix the cement composition. With the valve 58 closed and the drain valve 56 open, the fluid chamber 42 can then be pressurized with inert gas by opening the valve 88 and the valve 108 can be opened whereby the cement composition displaces the flush composition from the test cell and the annular space 159 in the test cell is filled with the cement composition. Thereafter, in order to remove excess cement composition from the test cell above and below the insert end plates 146 and 148, the valves 122 and 56 are closed, the drain valve 128 is opened and the water valve 24 is opened to flush water through the bottom of the test cell 12 and displace cement composition therefrom into the drain. The shut-off valves 24 and 128 are then closed and the same procedure is performed on the upper portion of the test cell by opening drain valve 56 and opening the water valve 26 to displace cement composition from the upper portion of the test cell 12. Thereafter, the cement composition remaining in the fluid chamber 42 as well as the cement composition in the conduit and valve system 48 can be flushed with water to prevent the fluid chamber 42, the pump 46, the flow meter 120 and the conduits and valves from being plugged with set cement composition. As will be understood, the pump 46 and flow meter 120 can each include bypass conduits and valves to isolate them when a cement composition is caused to flow to the test cell 12.

After the cement composition within the test cell 12 and the insert 142 therein has set and bonded to the rock core, the test cell 12 can be opened by removing the threaded closure 136 therefrom, removing the lock nut 182 from the filtrate tube 160 and then removing the insert assembly from the test cell. The insert assembly including the set cement and rock core can then be disassembled to remove the set cement and rock core whereby it can be visually inspected such as by sawing the set cement and rock core laterally and longitudinally so that the junction between the set cement and rock core can be examined. Also, a shear bond strength test to determine the strength of the bond between the set cement and the rock core which is well known to those skilled in the art can be conducted on a portion of the set cement and rock core. The term "cement composition" is used herein to mean any of various types sealing compositions which are suitable for well sealing applications including, but not limited to, hydraulic cement slurries, hardenable epoxide containing liquids, hardenable polymeric compositions, hardenable rubber containing compositions and the like.

As mentioned above, the fluid resistivity sensing apparatus is utilized to help determine the effectiveness of flush fluids in removing oil base drilling fluids and the filter cake formed therefrom from the rock core. Oil left in the test cell has a different resistivity than water and the presence or non-presence of oil can be detected accordingly.

The Methods

The methods of the present invention for simulating the conditions in a well bore before and after cementing therein are basically comprised of circulating a drilling fluid through a closed test cell containing a permeable rock core while maintaining a desired or typical pressure differential across the rock core until a layer of filter cake is formed on the rock core, circulating a filter cake removal fluid through the test cell to simulate the clean up of the well bore prior to performing cementing operations therein and then determining the condition of the rock core with respect to the effectiveness of the filter cake removal fluid thereon.

The condition of the rock core can be determined by removing the rock core form the test cell and visually examining the rock core or by sonically ascertaining the thickness of the layer of filter cake on the rock core after circulating the drilling fluid and filter cake removal fluid through the test cell. As mentioned above, the permeability of the rock core used can first be determined by circulating an aqueous fluid such as fresh water through the test cell while collecting filtrate from the rock core to thereby determine its permeability. Further, in accordance with the methods of this invention, a cement composition can be circulated into the test cell after a selected filter cake removal fluid has been circulated therethrough and the cement composition allowed to set in contact with the rock core. Thereafter the condition of the bond between the set cement and the rock core can be determined either visually or by conducting a shear bond strength test on the set cement and rock core.

The methods of the invention can also include the step of sonically ascertaining the thickness of the filter cake remaining between the rock core and the cement composition placed in the test cell before the cement composition sets. Also, when an oil based drilling fluid is utilized, the extent of removal of oil from the test cell by a selected flush fluid can be determined by measuring the electric resistivity of the fluid remaining in the test cell.

Thus, the present invention is well adapted to carry out the objects and attain the ends and advantages mentioned as well as those which are inherent therein. While numerous changes may be made by those skilled in the art, such changes are encompassed within the spirit of this invention as defined by the appended claims.

What is claimed is:

1. An apparatus for simulating the conditions in a well bore before and after cementing therein comprising:

a closable elongated test cell having at least one inlet connection and one outlet connection formed therein at opposite ends thereof;

a removable elongated insert disposed within said test cell containing an elongated hollow permeable rock core having a cross sectional periphery smaller than the inside cross section of said insert, the ends of said insert being closed by perforated plates which sealingly contact the ends of said rock core whereby a test fluid flowing through said test cell and through said insert contacts only the outside longitudinal surfaces of said rock core;

a filtrate tube having at least one opening therein disposed within the interior of said rock core and sealingly extending through said insert and through said test cell whereby filtrate from said test fluid which passes through said rock core by way of the permeability thereof flows out of said test cell by way of said filtrate tube to a place of collection;

first conduit and valve means connected to a source of at least one test fluid and to said inlet and outlet connections of said test cell for selectively circulating said test fluid through said test cell; and a pump disposed in said conduit and valve means for selectively causing said test fluid to flow through said conduit and valve means and said test cell at a selected flow rate.

2. The apparatus of claim 1 wherein said test cell, said insert and said hollow rock core are all cylindrical in shape.

3. The apparatus of claim 1 wherein said source of a test fluid is comprised of a closeable mixing chamber containing said test fluid and through which said test fluid can be circulated.

4. The apparatus of claim 3 which further comprises second conduit and valve means connected to a source of pressurized inert gas and to said mixing chamber whereby the pressure of said fluid circulated through said mixing chamber and said test cell can be selectively raised and lowered by introducing said pressurized inert gas into said mixing chamber or withdrawing said pressurized inert gas therefrom, respectively.

5. The apparatus of claim 1 wherein said removable insert and said perforated plates thereof are formed of a material to which set cement compositions do not adhere.

6. The apparatus of claim 5 wherein said material is selected from tetrafluoroethylene fluorocarbon polymers, fluorinated ethylene-propylene resins and copolymers of the aforesaid polymers and resins.

7. The apparatus of claim 1 wherein said test cell further comprises sonic means connected thereto for sonically measuring the thickness of filter cake formed on the outside surfaces of said rock core.

8. The apparatus of claim 1 wherein said test cell further comprises electronic means connected thereto for electronically measuring the resistivity of the fluid flowing through said test cell.

9. The apparatus of claim 1 which further comprises filtrate back-pressure control means connected to said filtrate tube.

10. A method of simulating the conditions in a well bore before and after cementing therein comprising the steps of:

(a) circulating an aqueous fluid through a closed test cell while collecting filtrate from a permeable rock core to determine the permeability thereof;

(b) circulating a drilling fluid through said test cell containing a removable insert and said rock core having a space therebetween while maintaining a selected pressure differential across said rock core until a layer of filter cake is formed on said rock core;

(c) circulating a filter cake removal fluid through said test cell to simulate the clean-up of said well bore prior to performing cementing operations therein; and then (d) determining the condition of said rock core with respect to the effectiveness of said filter cake removal fluid thereon by sonically ascertaining the thickness of said layer of filter cake on said rock core prior to and after the performance of step (c).

11. The method of claim 10 which further comprises the steps of:

(d) circulating a cement composition into said test cell and into said insert therein whereby said cement composition contacts the outside surfaces of said rock core including filter cake remaining thereon and fills said space between said rock core and said insert;

(e) allowing said cement composition to set; and (f) determining the condition of the bond formed between said set cement composition and said rock core.

12. The method of claim 11 wherein said cement composition is selected from the group of hydraulic cement slurries, hardenable epoxide containing liquids, hardenable polymeric compositions, hardenable rubber containing compositions and the like.

13. The method of claim 11 wherein the condition of said bond between said set cement and said rock core is determined in accordance with step (f) by removing said rock core and said set cement and visually examining said rock core and said set cement.

14. The method of claim 11 wherein the condition of said bond between said set cement and said rock core is determined in accordance with step (f) by sonically ascertaining the thickness of filter cake remaining between said rock core and said set cement.

15. The method of claim 11 wherein the condition of said bond between said set cement and said rock core is determined in accordance with step (f) by removing said rock core and said set cement bonded thereto and performing a shear bond test thereon to measure the strength of the bond between said rock core and said set cement.

16. The method of claim 11 wherein said drilling fluid is selected from the group of oil based and water based drilling fluids.

17. The method of claim 11 wherein said cement composition is an aqueous Portland cement slurry.

* * * * *